United States Patent [19]
Groppi, Jr. et al.

[11] Patent Number: 5,925,742
[45] Date of Patent: *Jul. 20, 1999

[54] PROTEIN AFFECTING $K_{ATP}$ CHANNELS

[75] Inventors: Vincent E. Groppi, Jr.; Martin R. Deibel, Jr., both of Kalamazoo; Mark L. Wolfe, Portage; Anthony W. Yem, Kalamazoo, all of Mich.

[73] Assignee: Pharmacia & Upjohn Company, Kalamazoo, Mich.

[ * ] Notice: This patent is subject to a terminal disclaimer.

[21] Appl. No.: 08/920,067

[22] Filed: Aug. 26, 1997

Related U.S. Application Data

[62] Division of application No. 08/341,401, Nov. 17, 1994, Pat. No. 5,856,449.

[51] Int. Cl.⁶ .................................................... C07K 14/00
[52] U.S. Cl. ...................... 530/395; 530/326; 530/402; 530/412; 530/418; 530/419; 530/427
[58] Field of Search .................................... 530/395, 326, 530/402, 412, 418, 419, 427

[56] References Cited

U.S. PATENT DOCUMENTS

| | | | |
|---|---|---|---|
| Re. 31,244 | 5/1983 | Petersen | 424/263 |
| 4,057,636 | 11/1977 | Petersen | 424/263 |

FOREIGN PATENT DOCUMENTS

| | | |
|---|---|---|
| 405525-A2 | 1/1991 | European Pat. Off. . |
| 9211233-A1 | 12/1990 | WIPO . |

OTHER PUBLICATIONS

H. J. Petersen, et al., "Synthesis and Hypotensive Activity of N–Alkyl–N"–Cyano–N'–Pyridylguanidines", J. Med. Chem., 21, 8, pp. 773–781 (1978).

*Primary Examiner*—Cecilia J. Tsang
*Assistant Examiner*—Abdel A. Mohamed
*Attorney, Agent, or Firm*—Thomas A. Wootton

[57] ABSTRACT

This invention describes the isolation and identification of a new protein, p56, useful for the identification of drugs that will selectively open or close K channels. The protein p56 has a molecular weight of about 56,000 daltons and the N-terminal peptide sequence is: Glu-Pro-Arg-Ala-Pro-Pro-Glu-Lys-Ile-Ala-Ile-Val-Gly-Ala-Gly-Ile.

6 Claims, 9 Drawing Sheets

PROTEIN AFFECTING $K_{ATP}$ CHANNELS

CROSS-REFERENCE TO RELATED APPLICATIONS

The present patent application is a divisional application of U.S. patent application Ser. No. 08/341,401 filed Nov. 17, 1994, now U.S. Pat. No. 5,856,449.

FIELD OF THE INVENTION

This invention relates to potassium channels and the proteins that comprise those channels.

INFORMATION DISCLOSURE

The following documents are related to the cyanopyridylguanidine compound used to isolate the protein disclosed herein.

Petersen, Hans J., et. al., "Synthesis and Hypotensive Activity of N-Alkyl-N"-cyano-N'-pyridylguanidines," *J. Med. Chem.*, 21, 8, pp. 773–781 (1978).

U.S. Pat. No. Re. 31,244, reissued May 17, 1983, "Antihypertensive Pyridylguanidine Compounds," H. J. Petersen.

U.S. Pat. No. 4,057,636, issued Nov. 8, 1977, "Antihypertensive Pyridylguanidine Compounds," H. J. Petersen.

WO 9211233-A1, published Dec. 19, 1990, "New aryl: cyano:guanidine potassium channel dilater—for treating hypertension," assigned to Kanebo Ltd.

European Patent 405 525 A2, published Feb. 1, 1991, "Novel Cyanoguanidine Derivatives," M. Tominori.

BACKGROUND

Ionic channels of cell membranes are the basic sites where ionic fluxes take place. The modern era of the study of drug-channel interactions began when voltage clamp techniques were used to demonstrate the block of Sodium, ($Na^+$), and potassium, ($K^+$), channels of squid axons caused by procaine and cocaine. Narahashi, *Ann Neurology* (1984); 16(suppl): S39–S51.

This invention concerns proteins which regulate or constitute the pore region of potassium channels. Potassium channels appear to be ubiquitous, found even in bacteria. See, R. Milkman, "An *Escherichia Coli* homologue of eukaryotic potassium channel proteins" *Proc. Natl. Acad. Sci. USA*, Vol 91, pp. 3510–3514, (1994). Pharmacological, biophysical and molecular studies have revealed multiple subtypes for membrane ion channels that form potassium selective pores in the plasma membrane of many mammalian cells. One method of classifying K channels is based on what regulates channel activity or function. For example, one class can be defined as K channels modulated by transmembrane voltage, another class modulated solely by calcium and/or nucleotides, and yet a third class modulated by G protein involvement. However, in a more simplistic manner, one can classify the family of K channels simply by their respective gating properties. In other words, a comparison of the pharmacological and electrophysiological properties of potassium channels has given rise to an operational definition for grouping the various subtypes based largely on their gating properties. At present, potassium channels of known amino acid sequence comprise two distantly related protein families. One of these channel families is termed, "voltage-gated," the other channel family is termed "inward rectifying."

The structure of the voltage-gated channel protein is known to be comprised of six membrane spanning domains in each subunit, each of which is regulated by changes in membrane potential. B. Hille. "Ionic Channels of Excitable Membranes" (Sinauer, Sunderland, Mass., 1992). Voltage-gated potassium channels sense changes in membrane potential and move potassium ions in response to this alteration in the cell membrane potential. Molecular cloning studies on potassium channel proteins has yielded information primarily for members of the voltage-gated family of potassium channels. Various genes encoding these voltage-gated family of potassium channel proteins have been cloned using Drosophila genes derived from both the Shaker, Shaw and Shab loci; Wei, A. et. al., *Science* (1990) Vol. 248 pp. 599–603.

Unlike the voltage-gated channel proteins with six membrane spanning regions, the inward rectifier channels have only two membrane spanning domains, each sensitive to changes in the net potassium concentration. Within this class of channels are the ATP-sensitive potassium channels. These channels are classified by their sensitivity to concentration fluxes in ATP. The ATP-sensitive, or ATP-gated, potassium channel is an important class of channels that links the bioenergetic situation of the cell to changes in cell function. These channels are blocked by high intracellular ATP concentrations and are open when ATP decreases. Lazdunski (1992); M. Lazdunski et al., "ATP-Sensitive $K^+$ Channels", *Renal Physiol. Biochem.* Vol. 17: pp. 118–120 (1994).

Although ATP-gated potassium channels were originally described in cardiac tissue; Noma, A. *Nature* (1983) Vol. 305 pp. 147–148, they have subsequently been described in pancreatic β-cells; Cook et. al., *Nature* (1984) Vol. 311 pp. 271–273, vascular smooth muscle; Nelson, M. T. et. al., *Am. J. Physiol.* (1990) Vol. 259 pp. C3–C18 and in the thick ascending limb of the kidney; Wang, W. et. al. *Am. J. Physiol.* (1990) Vol. 258, pp. F244–F-253.

The ATP-sensitive, or ATP-gated potassium channels play an important role in human physiology. The ATP-sensitive potassium channel, like other potassium channels, selectively regulate the cell's permeability to potassium ions. These channels function to regulate the contraction and relaxation of the smooth muscle by opening or closing the channels in response to the modulation of receptors or potentials on the cell membrane. When ATP-sensitive potassium channels are opened, the increased permeability of the cell membrane allows more potassium ions to migrate outwardly so that the membrane potential shifts toward more negative values. When the membrane potential shifts toward more negative values the opening of the voltage-dependent calcium channels is reduced, this reduces the influx of calcium ions into the cell because the calcium channels become "increasingly less open" as the membrane potential becomes more negative. Consequently, drugs having ATP-sensitive potassium channel opening activity, drugs known as potassium channel openers, can relax vascular smooth muscle and are useful as hypotensive and coronary vasodilating agents. In contrast, drugs having ATP-sensitive potassium channel blocking activity, drugs known as potassium channel blockers, inhibit ATP-sensitive potassium channels by decreasing potassium efflux, leading to membrane depolarization which opens voltage-gated $Ca^{2+}$ channels. Arkhammar et al. (1987) "Inhibition of ATP-regulated $K^+$ channels precedes depolarization-induced increase in cytoplasmic free $Ca^{2+}$ concentration in pancreatic B-cells", *J. Biol. Chem.* 262: 5448–5454. These drugs find optimal use in the stimulation of insulin secretion in type II diabetes mellitus.

A relatively large number of compounds are now known which open cell membrane ATP-sensitive potassium channels, particularly in smooth muscle: minoxidil sulfate, diazoxide and nicorandil are well known potassium channel openers. The target site for these agents is presumably on the potassium channel itself, but may also be on an associated regulatory protein. Isolation of the target site for the potassium channel openers would allow for protein sequence analysis and cloning of those potassium channel opener proteins. Similar analyses of drug binding proteins in $K_{ATP}$ channels have been performed for the class of K channel blockers such as glyburide. Sulfonylurea receptors have been analyzed on a variety of cell and tissue types using a photoactivable form of glyburide. Aguilar-Bryan, L., et al., "Photoaffinity Labeling and Partial Purification of the B Cell Sulfonylurea Receptor Using a Novel, Biologically Active Glyburide Analog", *J. Biol. Chem.* (May 15, 1990) Vol. 265, pp. 8218–8224.

Potassium channel openers represent a widely diverse series of compounds which all have the reported effect of opening only a subset of channels described as sensitive to ATP. As explained above, these compounds cause physiological responses by increasing membrane permeability to potassium, this leads to hyperpolarization of the cell membrane and temporal desensitization to electrical and chemical stimuli.

Openers which target these channels have been synthesized as possible drugs in hypertension, angina pectoris, coronary heart disease, asthma, and urinary incontinence. Blockers which target these channels include the sulfonylureas, such as glyburide. The latter is an example of an important drug which targets $K_{ATP}$ channels in the pancreas, thus providing a treatment for non-insulin dependent diabetes mellitus.

The rationale for the effectiveness of these drugs in targeting the $K_{ATP}$ channel resides in the fact that this channel constitutes the main resting conductance in the B-cell. Depolarization of the channel by the sulfonylurea blockers ultimately results in insulin release.

Despite the apparent selectivity afforded by such drugs, it also appears true that openers have multiple effects on target cells as well as selective effects on several tissue types. K. Lawson and P. E. Hicks, "Potassium Channel Openers: Pharmacological Anomalies Suggest Heterogeneous Sites of Action", (1993) *Curr. Opin. Invest. Drugs* Vol 2 pp. 1209–1216. It is the latter effect, that of multiple tissue targeting, that has reduced the importance of the K channel openers as selective marketable drugs. It is essential to understand what confers selectivity of drugs to specific organs before a systematic approach can be made towards drug design.

The membrane proteins which bind to potassium channel openers are believed to be structurally related, although it isn't clear whether drug selectivity is imparted by the channel protein itself or by the contribution of accessory proteins. These proteins, which bind to selective drugs, may be novel K channels or they may be one of several K channel accessory proteins that act in concert with the primary K channel protein and that are needed by the system for the proper physiological response.

An analogous system using the channel blocker, glyburide, has been explored for pancreatic B cell $K_{ATP}$ channels. Aguilar-Bryan, L., et al., "Co-Expression of Sulfonylurea Receptors and $K_{ATP}$ Channels in Hamster Insulinoma Tumor (HIT) Cells: Evidence for direct association of the receptor with the channel", *J. Biol. Chem.* (1992), Vol. 267 pp. 14934–14940.

This invention describes the isolation and identification of a new protein, p56, useful for the identification of selective drugs that will selectively open or close K channels. P56 is the first high affinity cyanoguanidine binding protein to be identified using a K channel opener photoactivable probe. Unexpectedly, this opener was shown to only bind to P56 in intact cells.

SUMMARY OF THE INVENTION

This invention comprises a glycoprotein of about 54,000 to 60,000 daltons and having an apparent core protein mass (free of sugars) of about 51,000 daltons, capable of being isolated from rat A10 cells and capable of binding with N-(3-azido-5-iodophenyl)-N'-cyano-N"-(1,1-dimethylpropyl)-guanidine. A glycoprotein having $K_{ATP}$ channel activity either by itself or in membranes with other $K_{ATP}$ channel proteins. A glycoprotein of about 56,000 daltons. A glycoprotein where the average mass of the individual sugars is about 2,500 daltons. A glycoprotein having at least three sites of N-linked glycosylation. A glycoprotein comprising the N terminal sequence of "Glu-Pro-Arg-Ala-Pro-Pro-Glu-Lys-Ile-Ala-Ile-Val-Gly-Ala-Gly-Ile-." A glycoprotein wherein the purified protein is the human homolog. A glycoprotein wherein the purified protein is the murine homolog. A glycoprotein having the characteristics of the p56 protein identified herein. An essentially pure glycoprotein as described herein.

Figure 1:
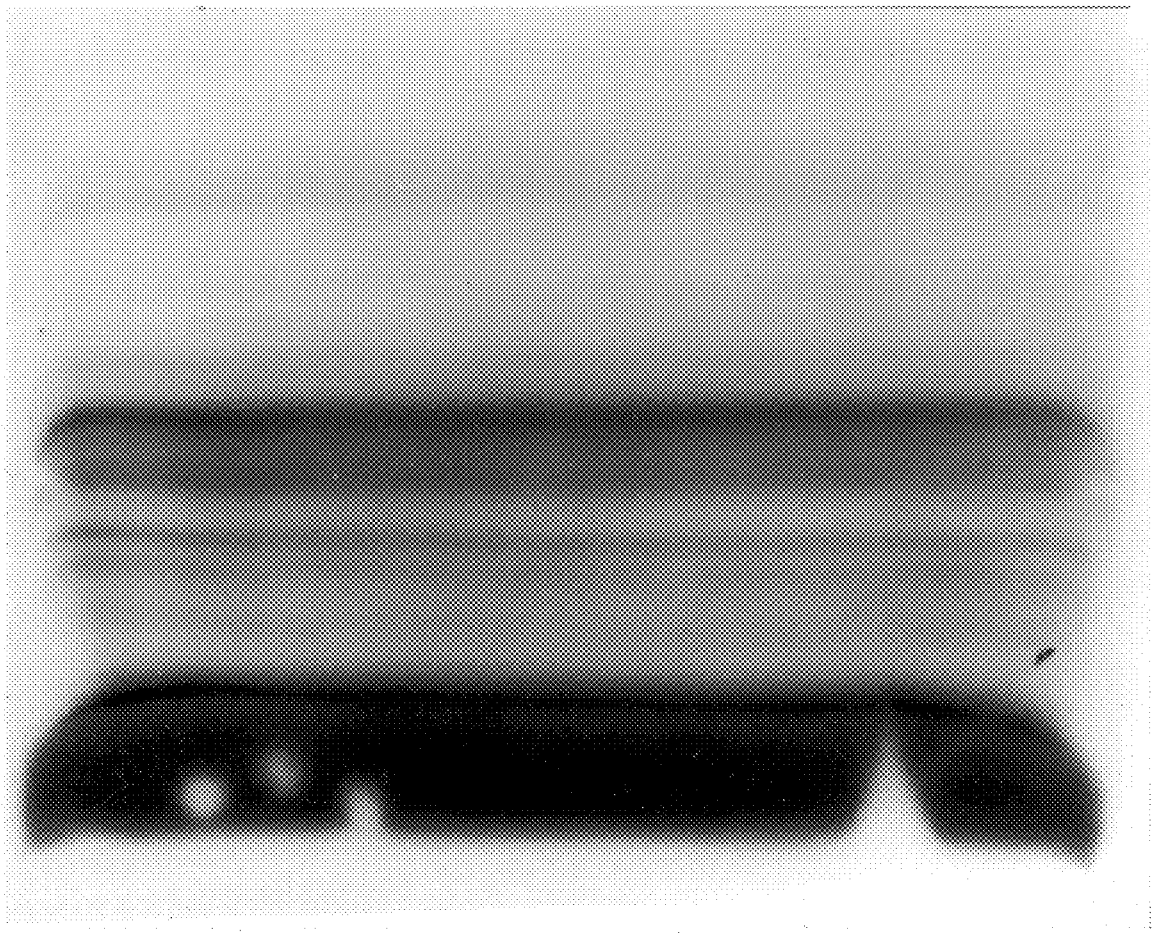
FIG. 1. Autoradiogram of a polyacrylamide gel showing the p56 protein at about 56,000 daltons.

ADDITIONAL DESCRIPTION OF THE INVENTION AND DESCRIPTION OF THE PREFERRED EMBODIMENTS

The following definitions and equipment sources, are provided:

Hour is h or hr. Minute is min. Milliliters is ml. DTT is dithiothreitol; it is purchased from any of several chemical suppliers. SDS is sodium dodecyl sulfate; the electrophoresis purity reagent supplier is Bio-Rad Laboratories, Richmond, Calif. All electrophoresis equipment was also purchased from the same vendor. NP40 is nonidet P40, a non-ionic detergent available from several chemical suppliers. HF is hydrogen fluoride/para-cresol (4-methylphenol)/para-thiocresol.

All chromatography buffers and solvents were obtained from various chemical suppliers and were of the highest grade obtainable; all water used in experiments was purified using a Milli-Q water purification/filtration system obtained from Millipore Corporation.

The YM10 or YM30 membranes used for ultrafiltration concentration were produced exclusively by Amicon, Danvers, Mass. X-OMAT AR scientific imaging films, are made by Eastman Kodak Company, Rochester, N.Y.

Recombinant N-glycanase enzyme is obtained from Genzyme Corporation, Cambridge, Mass. The deglycosylation reactions were conducted as suggested by the manufacturer, who provide buyers a data sheet and suggested protocol. Peptide conjugation to KLH (Keyhole Limpet Hemocyanin), was conducted using the Inject Immunogen Kit obtained from Pierce, Rockford, Ill.

Electrophoresis equipment was purchased from Bio-Rad Laboratories. (ABI) 476A protein sequencer (Applied Biosystems, Inc., Foster City, Calif.). PVDF solid matrix is Immobilon-P Transfer Membrane obtained from Millipore Corporation, Bedford, Mass. SMART micropurification chromatography system (Pharmacia LKB Biotechnology, Uppsala, Sweden); chromatography columns used with this system are available through several manufacturers.

Amino acid residues referred to in this application are listed below, they may also be given either three letter or single letter abbreviations, as follows:

Alanine, Ala, A; Arginine, Arg, R; Asparagine, Asn, N; Aspartic acid, Asp, D; Cystein, Cys, C; Glutamine, Gln, Q; Glutamic Acid, Glu, E; Glycine, Gly, G; Histidine, His, H; Isoleucine, Ile, I; Leucine, Leu, L; Lysine, Lys, K; Methionine, Met, M; Phenylalanine, Phe, F; Proline, Pro, P; Serine, Ser, S; Threonine, Thr, T; Tryptophan, Trp, W; Tyrosine, Tyr, Y; Valine, Val, V; Aspartic acid or Asparagine, Asx, B; Glutamic acid or Glutamine, Glx, Z; Any amino acid, Xaa, X.

All amino acids have a carboxyl group and an amino group. The amino group of the amino acid is also referred to as the "N-terminus" of the amino acid. The carboxyl group of an amino acid is also referred to as the "C-terminus" of the amino acid. The "N-terminus" of an amino acid may form a peptide bond with a carboxyl group of another compound. The carboxyl group that combines with the "N-terminus" of an amino acid may be the carboxyl group of another amino acid or it may be from another source. If several amino acids are linked into a polypeptide, then the polypeptide will have a "free" N-terminus and a "free" C-terminus.

The materials and methods used to isolate, identify and characterize the protein are provided.

Materials. The cyanoguanidine, N-(3-azido-5-iodophenyl)-N'-cyano-N"-(1,1-dimethylpropyl)-guanidine, a K channel opener utilized for photoaffinity labelling, is synthesized. The synthesis is according to the procedures described in U.S. Pat. No. 5,525,742, issued Jun. 11, 1996, Gadwood, et. al., Azidophenylcyanoguanidine and Their Use as Photoaffinity Probes. The designated compound contained an aryl azide radiolabelled with [$^{125}$I] to a specific activity of 2200 Ci/mmole. (New England Nuclear).

Electrophoresis. One-dimensional analytical SDS polyacrylamide gel electrophoresis is conducted using 10% gels in a mini Protean II system (Bio-Rad Laboratories) according to the method of Laemmli, U. K. Laemmli, (1970) Nature, Vol. 227, pp. 680–685, adjusted with minor modifications. Before electrophoresis samples are diluted 1:1 with denaturation buffer (2% SDS, 25% glycerol, 0.25 M Tris HCl, pH 6.8, and 1% β-mercaptoethanol). Electrophoresis is conducted at constant power (5 watts/gel) for 1 hour at room temperature and terminated when the dye front (bromphenol blue) reaches the bottom of the gel. The completed gels are either electroblotted onto nitrocellulose or PVDF, or fixed in 50% ethanol and 10% acetic acid, and stained with Coomassie Brilliant Blue G-250.

Analysis of Radiolabelled Proteins (Assay Method). Radiolabelled fractions may be analyzed in several ways depending on the state of the sample. For solution samples, simply count a portion or all of the sample in a gamma counter (0.5 to 1.0 min per sample). For wet gels, incubate the gels in a −70° C. freezer with XOMAT AR x-ray film, or cut the gel into 2 mm pieces and count the sections in a gamma counter. For dried gels or dried blot papers, a phosphorimager (Molecular Dynamics) for quantitation of the individual bands may be used.

A10 Cell Growth, Photoaffinity Labelling, Membrane Preparation. A10 cell lines derived from embryonic rat aorta are obtained from the American Type Culture Collection (CRL-1476). The cells are subcultured and grown to confluence in Corning 150 mm tissue culture plates at 37° C. in 6.0% $CO_2$ in Dulbecco's Modified Eagle's Medium supplemented with 20% (v/v) fetal bovine serum. The cells are then washed 2× with Earle's balanced salt solution buffered to pH 7.4 with 20 mM HEPES (EBSS-H). The cells are placed in EBSS-H containing 10 nM [$^{125}$I]-U-97149. The A10 cells are equilibrated with the radiolabeled compound for 15 min at 37° C. The A10 cells are then placed on ice for 2 min and exposed to 600 µwatts/cm$^2$ of 254 nm UV light.

After photolysis, the A10 cells are washed extensively with phosphate buffered saline. Membranes from the A10 cells are solubilized in a cocktail of 0.2% Triton X-100 detergent and 20 mM Tris pH 6.8 and protease inhibitors (10 µg/ml leupeptin, 10 µg/ml aprotinin, 10 µg/ml pepstatin, and 5 mM benzamidine). The membranes are precipitated with 4 volumes of ice cold acetone for 60 min on dry ice. The precipitated membrane proteins are collected by centrifugation at 20,000 rpm for 30 min at 4° C. in a Beckman SW-28 rotor. After centrifugation the supernatant is discarded and the pellet is dissolved in 1% SDS and 10 mM βME.

Purification of the protein p56. Preparative SDS PAGE—Triton solubilized [$^{125}$I]-CG-labelled A10 membrane protein preparations from 24–48 large culture plates are acetone precipitated and washed. The resulting pellets are resolubilized in 1% sodium dodecyl sulfate (SDS) containing 10 mM dithiothreitol (DTT) (approximately 6–12 ml final volume) as described above. An equal volume of sample denaturation buffer is added (125 mM Tris, HCl pH 6.8, 1% SDS, 10 mM DTT), and after mild heating and mixing, the sample is distributed onto 4 preparative polyacrylamide gels (10% total; 37.5:1.0 acrylamide to bis-acrylamide ratio; 1.5 mm thickness). These gels are run according to the method of Laemmli with minor modifications in a Protean II cell at low voltage (25–30 V limited) overnight at room temperature. The upper tank buffer is supplemented with 1 mM sodium thioglycollate to reduce possible protein modification due to oxidation or free radicals within the gel and to keep the proteins in reduced form during the run to prevent disulfide linked aggregation.

Upon completion of electrophoresis, both the dye front, which consists mainly of free drug, and one of the major proteins, actin, are visualized by incubation of the completed gels in a solution of 0.1 M potassium chloride for about 5 min. Following brief washings in deionized water, the position of actin is marked and the bottom of the gel is cut to allow for recognition patterns on developing autoradiograms. Each gel is wrapped in saran wrap and sealed in plastic bags. Autoradiograms are made after 2–3 h exposure (−70° C.) of the wet, frozen gels to X-OMAT AR films. These autoradiograms are then used as a guide for the excision of the target protein band; in this case, p56. The excised polyacrylamide gel strips are minced and fragmented using a mortar and pestle, and incubated in a large volume of 1% SDS containing 10 mM DTT (~500 ml). After a 2 hour incubation with stirring, the solution is centrifuged at low speed in 50 ml tubes for 5 min. at room temperature. The supernatant is removed and poured through a 0.22 micron filter to remove remaining polyacrylamide fines. The resulting solution is concentrated by Amicon ultrafiltration (YM-30 membrane) to a final volume between 6 and 12 ml.

Reverse Phase Chromatography. The concentrate from the above preparative SDS PAGE extract of p56 is injected onto a 0.46×15 cm (10μ) biphenyl HPLC column. The column profile is developed with a gradient of 32% to 54.4% acetonitrile in 0.1% triflouroacetic acid over a period of 40 min at a flow rate of 1 ml/min (1 ml fractions are collected). A radioactivity profile is obtained of individual fractions by gamma counting at 0.5 min each for [$^{125}$I]. Appropriate fractions representing p56 as judged by SDS PAGE and blotting, followed by phosphorimaging to conclusively show the location of p56 in the resolved fractions, are pooled and dried by vacuum centrifugation (SpeedVac Evaporator/Concentrator System, Savant Instruments, Inc., Farmingdale, N.Y.).

Deglycosylation of p56. The biphenyl reverse phase HPLC purified p56 sample is redissolved in minimal 1% SDS, and heated in boiling water for 2 min. After heating, the sample is treated with the non-ionic detergent, NP-40, such that for each 1% of SDS, a minimum of 1.5% of NP-40 is added. This solution is incubated in sodium phosphate, pH 7.0, and is mixed with N-glycanase (Genzyme) as suggested by the manufacturer. The deglycosylation is allowed to proceed overnight at 37° C.

Microbore (SMART) HPLC. In some instances, samples after deglycosylation are further resolved on a microbore biphenyl column (2.7 mm×15 cm) on a SMART system (Pharmacia-LKB) at 100 μl/min.

Electroblotting. Transferral of proteins from SDS gel to Immobilon-P Transfer Membrane (PVDF; Millipore Corp., Bedford, Mass.) is performed with a semi-dry blotter at ~15 mA/cm$^2$ for 15 min.

Sequence analysis. N-terminal sequencing of the deglycosylated p56 protein electrophoretically transferred to PVDF, see, P. Matsudaira (1987) *J. Biol. Chem.* Vol. 262 pp. 10035–10038, after purification by SDS-PAGE, is performed on an Applied Biosystems Inc. (ABI) Model 476A protein sequencer.

Synthesis of the N-Terminal Peptide. Solid phase peptide synthesis (Barany & Merrifield, 1979, in The Peptides, Vol. 2, pp. 1–284, E. Gross and J. Meienhofer, editors, Academic Press, New York) is performed at 0.5 mmole scale utilizing Boc-Cys(4-CH$_3$Bzl)OCH$_2$ Pam resin (Applied Biosystems Inc., Foster City, Calif.) on an Applied Biosystems Inc. 430A Peptide Synthesizer. Amino acids may be obtained from any commercially available source. In the examples shown here all amino acids were obtained from Applied Biosystems Inc. The t-butyloxycarbonyl (BOC) group is used as the N-amino protecting group during step-wise synthesis. Trifunctional amino acid side chains are protected as follows: Arg(Tos), Glu(OBzl), and Lys(Cl-z). Each residue is coupled twice, then capped with acetic anhydride before the next cycle of synthesis. Quantitative ninhydrin tests are performed at each cycle of the synthesis. After removing the N-terminal Boc group in the usual fashion, the peptide is cleaved from the resin by treatment with Hydrofluoric acid (HF)/p-cresol/p-thiocresol (10:0.5:0.5) for 1 hour at −20° to −5° C.

The peptide resin is titrated with ether, the crude peptide dissolved in 50% acetic acid and the resin removed by filtration. The filtrate is evaporated to dryness under reduced pressure and lyophilized from glacial acetic acid. The crude peptide is purified by preparative reverse phase chromatography on a Vydac C-18 column (250×22.5 mm) using a water acetonitrile gradient, with each phase containing 0.1% TFA. Clean fractions, as determined by analytical HPLC, are pooled and acetonitrile evaporated under reduced pressure; an aqueous solution of the pooled fractions is lyophilized. The purified peptide is characterized by time of flight mass spectroscopy. The anticipated (M+H)+ is 1878.9.

Preparation of N-Terminal p56 Polyclonal Antibody. The N-terminal peptide, prepared above, is conjugated to KLH-maleimide (Pierce Chemical Co.), using procedures supplied by the manufacturer, to form the KLH-peptide conjugate at a final concentration of 4.0 mg/ml (KLH) and 2.7 mg/ml (peptide). Verification of coupling is made using Ellman's reagent. The KLH-peptide conjugate is separated from the free peptide by dialysis versus 1× PBS, pH 7.5. At the same time, a peptide conjugated to ovalbumin is prepared in an identical manner to provide for a sample which could be used to screen the test and production bleeds as they are produced. For the latter, the peptide-ovalbumin conjugate exhibited an apparent molecular weight of 60–65,000, compared to 45,000 for the unconjugated ovalbumin protein.

To test whether the rabbit sera is immunoreactive with the peptide, Western blots are conducted on nitrocellulose strips containing the ovalbumin-peptide conjugates at various concentrations. The primary sera are tested at a 1:100 dilution in TN buffer (20 mM Tris HCl, pH 7.5, 0.5 M NaCl) containing 1% BSA as carrier. The secondary antibody consists of dilute solutions of alkaline phosphatase-conjugates of goat-anti-rabbit IgG in TN buffer, supplemented with 1% BSA as carrier. Positives on the blots are visualized using AP substrates, NBT (p-nitroblue tetrazolium chloride) and BCIP (5-bromo-4-chloro-3-indolyl phosphate). To test whether the sera are capable of detecting p56 on blots, subject crude, partially purified and purified p56 samples to SDS polyacrylamide gel electrophoresis (10%), and blot onto nitrocellulose, as defined above. The blots are then probed using primary sera which had either been pre-adsorbed with the free N-terminal synthetic peptide or left unchallenged.

The following documents, incorporated by reference, also contain useful methods generally known to one skilled in the art: U. K. Laemmli (1970) *Nature* 227:680–685 and P. Matsudaira (1987) *J. Biol. Chem.* 262:10035–10038.

UTILITY OF THE INVENTION

This invention describes the isolation and identification of a new protein, p56, useful for the identification of drugs that will selectively open or close K channels. The p56 protein is the first high affinity cyanoguanidine binding protein to be identified using a K channel opener photoactivable probe. Unexpectedly, this opener was shown to only bind to p56 in intact cells, supporting the role of this protein in native potassium channel activity.

The p56 protein is likely to be a $K_{ATP}$ channel or an accessory protein that regulates $K_{ATP}$ channel activity. As an accessory protein in the channel, it would likely impart selectivity and specificity towards binding of potassium channel directed drug molecules. In either case, as a channel or accessory to a channel, p56 is an important and novel drug target.

The identification of a larger portion of the amino acid sequence will lead to the design of oligonucleotide probes which will permit the cloning of p56 from various species and expression of the p56 protein in bacterial and mammalian cell systems. An analogous approach has been taken by Bryan et al. in the isolation, characterization, and cloning of the glyburide receptor in HIT cells. Bryan, J., Aguilar-Bryan, L., and Nelson, D., "Cloning of a Sulfonylurea Receptor (ATP-Sensitive K+ Channel ?)" from Rodent a- and B- Cells, *First International Conference on ATP-Sensitive K+ Channels and Sulfonylurea Receptors* (Sep. 30–Oct. 1, 1993), Houston, Tex., pp. 149–153.

Knowledge of the amino acid sequence for p56 will allow the design of appropriate oligonucleotide probes for determination of mRNA levels in cell and tissue preparations using in situ hybridization experiments. Knowledge of the sequence will also allow the examination of the structure of the protein by computational software programs, providing a direct method for primary and secondary structure comparison of p56 to known potassium channel proteins.

The identification of this protein will allow the design of higher affinity polyclonal antibodies and/or monoclonal antibodies to be developed that recognize p56 in different species. Such antibodies will allow cell and tissue distribution of the protein to be determined. Antibodies to the p56 protein will allow for immunocytochemistry and histological examination of p56 protein expression in cells and tissue sections to complement the analysis of mRNA levels by Northern blot analysis.

This system can be used to study how potassium channel openers and blockers interact with the channel complex by competition studies, and to study and identify the other members of the potassium channel complex.

Additional understanding of the utility of the invention can be found in the following documents, incorporated by reference: U. Quast (1993) "Do the K+ Channel Openers Relax Smooth Muscle by Opening K+ Channels ?", *Trends In Pharmaceutical Sciences* 14:332–337. U. Quast, K. M. Bray, H. Andres, P. W. Manley, Y. Baumlin, and J. Dosogne (1993) Binding of the K+ Channel Opener, [³H] P1075 in rat isolated aorta: Relationship to functional effects of openers and blockers. *Molecular Pharmacology* 43:474–481. D. R. Howlett and S. D. Longman (1992) Identification of a binding site for [³H] cromakalim in vascular and bronchial smooth muscle cells. *British J. Pharmacol.* 107:396P. Barany, Merrifield (1979) in The Peptides (Gross, E., and Meienhofer, J., eds.), Vol. 2, pp.1–284, Academic press, New York.

DETAILED DESCRIPTION OF THE INVENTION

The present inventors have isolated and purified a unique protein called p56. This protein is either a true K channel protein or an accessory protein which might confer selectivity to a given channel. The N-terminus of the protein has been determined and a peptide representing the N-terminus of the N-deglycosylated p56 was synthesized. Polyclonal antibodies to the peptide were created which immunoreact with both the free peptide as well as authentic p56 protein.

Radiochemically labelled and photoactivable K channel openers are used to identify cyanoguanidine binding proteins in a membrane preparation of A10 cells. One suitable probe is N-(3-azido-5-iodophenyl)-N'-cyano-N"-(1,1-dimethylpropyl)-guanidine, see formula 1, below.

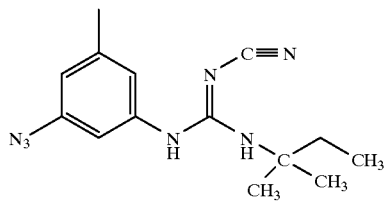

Formula 1

The proteins in the A10 cell preparation are first photolabelled, and then the cells are extracted with a cocktail of 0.2% Triton X-100 detergent and 20 mM Tris HCl, pH 6.8, containing protease inhibitors (10 ug/ml leupeptin, 10 ug/ml aprotinin, 10 ug/ml pepstatin, and 5 mM benzamidine). A cold solution of acetone is added to the Triton extract to precipitate the proteins, and allow for the removal of the unreacted photoaffinity label in the supernatant. Proteins present in the acetone pellet, including those radiolabelled proteins which were photolabelled, were then extracted with 1% sodium dodecyl sulfate (SDS) containing 10 mM dithiothreitol or 10 mM 2-mercaptoethanol.

Preliminary studies of the protein, p56, showed that the solubility of the protein was lost in the absence of SDS. However, use of SDS solutions of crude membrane proteins was found ineffective for purification using several reverse phase columns (C4 or C18). A common problem was the resolution of entire micellar products containing several different sized proteins, without significant purification afforded. To avoid these problems, we chose a biphenyl HPLC chromatography step, since this column accommodates solutions of 1% SDS, allows for resolution of SDS-dissolved proteins, and doesn't result in broadening effects noted in C4 and C18 column profiles.

Therefore, since the presence of SDS in the sample could be tolerated prior to HPLC resolution, we preferred to first select for the size range of proteins which are approximately 56 kilodaltons by preparative SDS PAGE as described in the Methods section. This method effectively removes the contaminating radiolabelled proteins which are either lower or higher molecular weight than p56. A resulting autoradiogram of a typical wet gel after 2 hours incubation with X ray film at −70° C. shows a complex pattern of radiolabelled proteins, with a major labelled protein easily detected at 56,000 daltons, see FIG. 1. The Y-axis of this illustration depicts the molecular weight, with the bottom representing the location where the smallest proteins migrate and the top representing the location where the largest proteins migrate (the relationship of migration distance to molecular weight is a logarithmic function). For these studies we commonly utilized 10% polyacrylamide (37.5:1.0 acrylamide:bis-acrylamide), resulting in an effective range of separation of proteins having masses from 15 kilodaltons through 200 kilodaltons.

The relative molecular weight of p56 was determined by comparison of its migration to that of a series of proteins having known masses. The predicted mass is determined following a linear regression analysis of the migration distances of the known standard proteins versus their molecular masses. When the mass of p56 is calculated by this method, an average mass of 56 kD is measured, with variability of the measurement limiting the size from 54 to 60 kD.

FIG. 1 shows that there are several radiolabelled bands present on the gel making it difficult to discern specific from non-specific radiolabelling. However, we know that the p56 band is specific since excess cold drug competition results in loss of detectable radioactivity at this position (data not shown). The major band noted at 56,000 daltons on the gel (as located by the autoradiogram) was excised and extracted out by passive diffusion in a 1% solution of sodium dodecyl sulfate containing 10 mM dithiothreitol. The resulting solution was concentrated to a small volumes (less than 8 ml) by ultrafiltration (Amicon Corporation, Lexington, Mass.).

Figure 2:
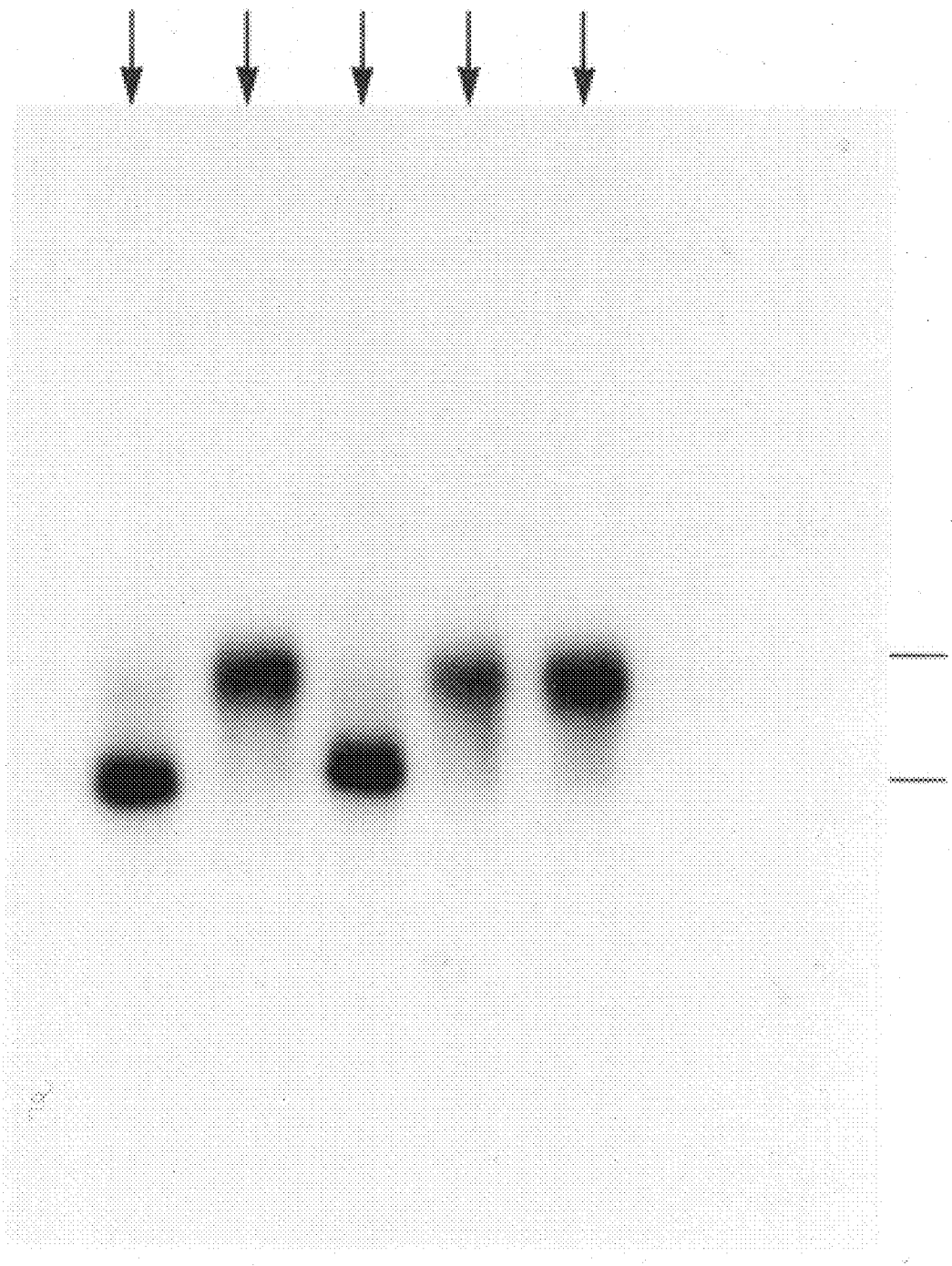
FIG. 2 The p56 protein after digestion with N-glycanase, endoglycosidase H, endoglycosidase F, and a combination treatment of neuraminidase and O-glycanase.

A determination of whether p56 is a glycoprotein was made by digesting the SDS extracted protein solution with N-glycanase, endoglycosidase H, endoglycosidase F, and a combination treatment of neuraminidase and O-glycanase. The results of experiments with a partially purified preparation of [$^{125}$I] p56 using these enzymes are shown in FIG. 2. FIG. 2 shows the results of digestion of p56 (left to right) with: N-glycanase (Lane 1), O-glycanase+Neuraminidase (Lane 2), Endo H (Lane 3), Endo F (Lane 4), and Control (Lane 5).

Results show that p56 is sensitive only to Endo H and N-glycanase (as judged by a demonstrated change in migration of the radiolabelled band on the gel), suggesting that the protein contains one or more sites of N-linked glycosylation of a high mannose type. The negative results with neuraminidase and O-glycanase suggested no O-linked glycosylation or sialic acid residues present in the glycoprotein.

The deglycosylation pattern of p56 was examined with variable concentrations of N-glycanase. Analysis indicates that in addition to p56 and its fully deglycosylated product (p52), there are at least two intermediate forms of glycosylated p56. We thus conclude that there are at least three sites of N-linked glycosylation on the p56 protein isolated from A10 membranes.

Purification and Characterization of p56.

Starting with a concentrate of the sodium dodecyl sulfate extraction of p56 from gel slices, radiolabelled as a consequence of reacting with the photoactivatable K channel opener, as explained above, the sample is applied onto a biphenyl reverse phase column.

Figure 3A:
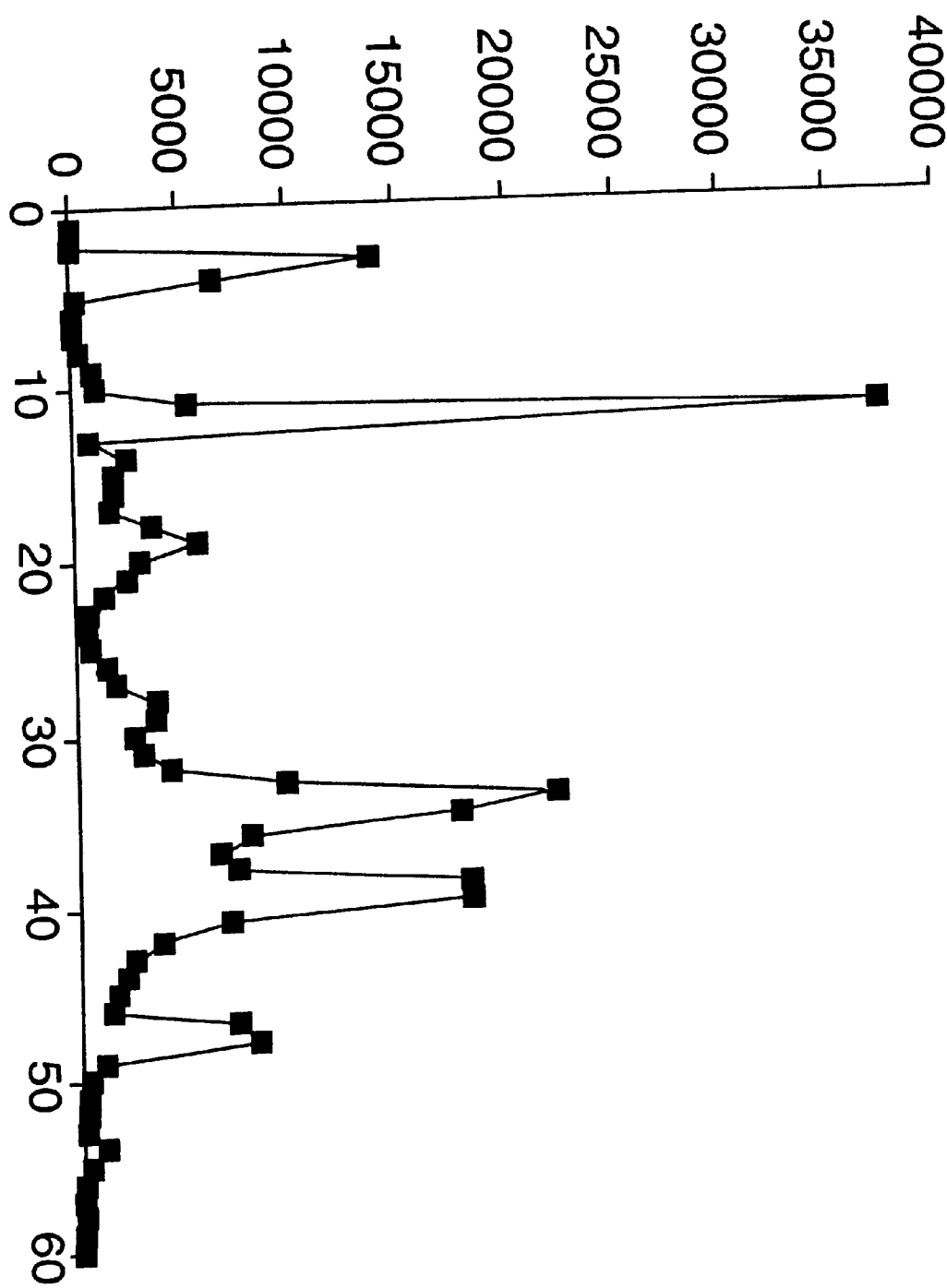
FIGS. 3A and 3B Typical column profile of sodium dodecyl sulfate extraction of p56 applied onto a biphenyl reverse phase column.
Figure 3B:
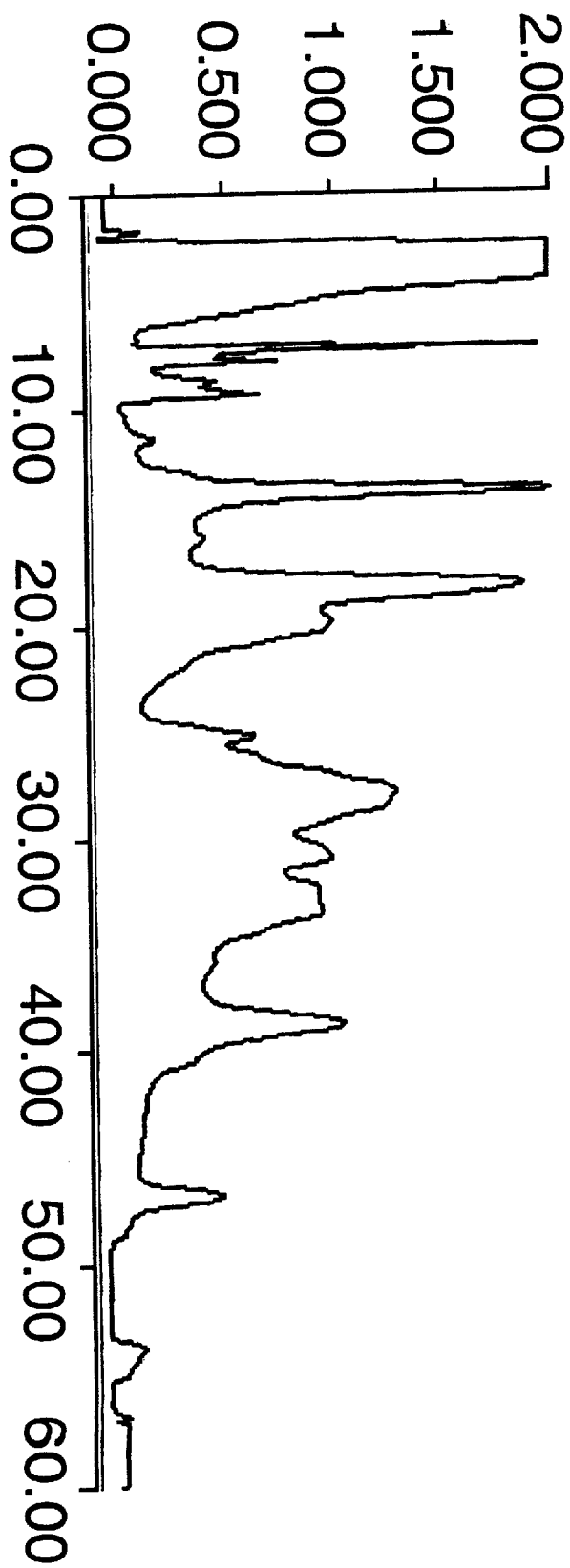
Figure 4A:
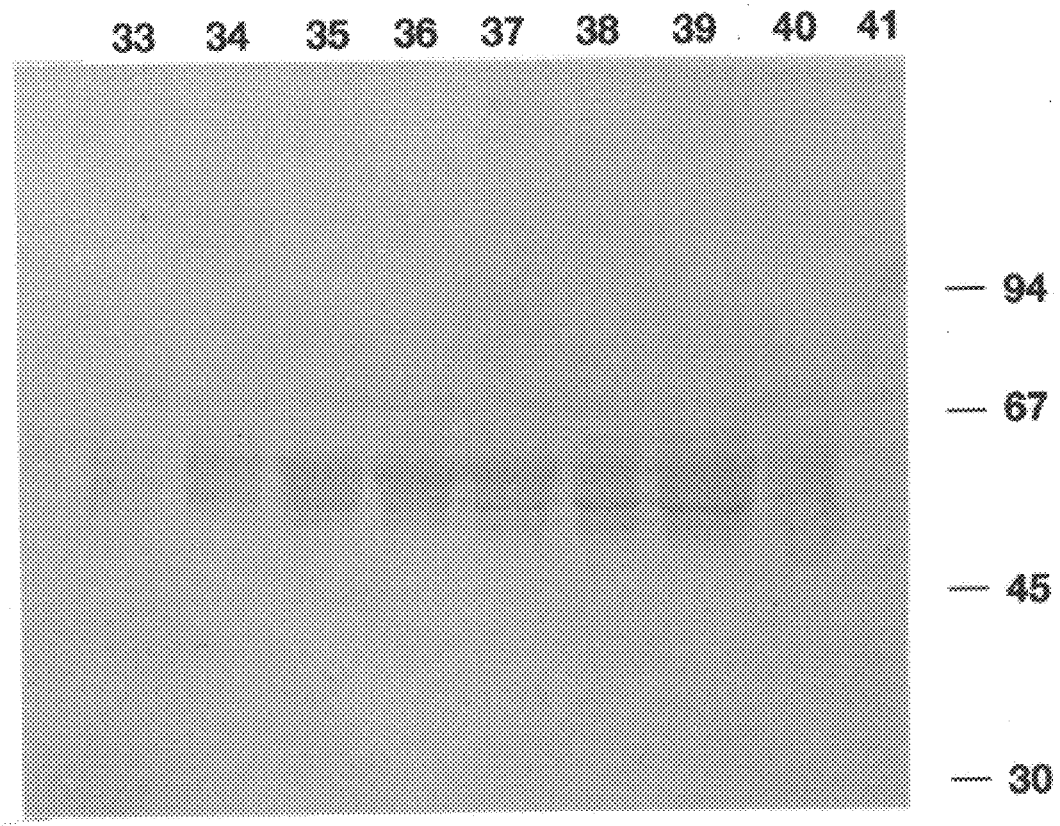
FIG. 4 SDS PAGE (FIG. 4A) and autoradiography (FIG. 4B) of selected fractions from a biphenyl reverse phase column.
Figure 4B:
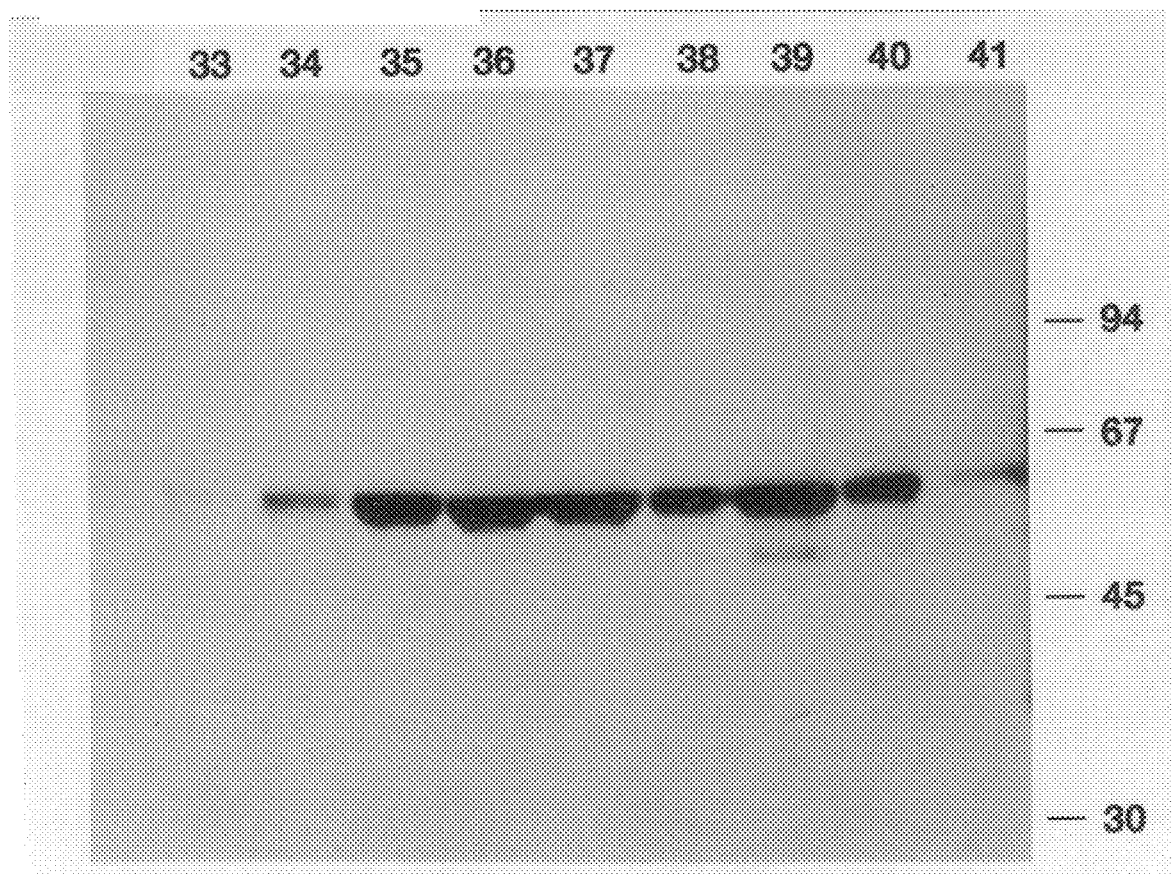

A typical column profile is shown in FIGS. 3a and 3B. FIG. 3A shows the radioactivity profile (X axis is retention time as column fractions; Y axis=CPM), and the profile of the absorbance of the sample is shown in FIG. 3B (X axis=Retention Time; Y axis=Absorbance at 215 nm [$A_{215}$]). The latter absorbance represents the most sensitive region of the absorption profile of proteins, indicative of peptide bonds. An examination of the selected fractions from this step by SDS PAGE is shown in FIGS. 4A and 4B. FIG. 4A shows the stained polyacrylamide gel, while an autoradiogram of the same gel is shown in FIG. 3B. The data shows the protein and radiochemical and protein purity, respectively, at this stage of the purification process. The p56 protein, defined by radioactivity and size, is noted in fractions 33–41. Appropriate fractions are selected and dried by vacuum centrifugation. The dried sample is redissolved in SDS containing buffer and subjected to deglycosylation with N-glycanase. The product of this step results in a p56 protein which is now devoid of N-linked oligosaccharides.

Figure 5:
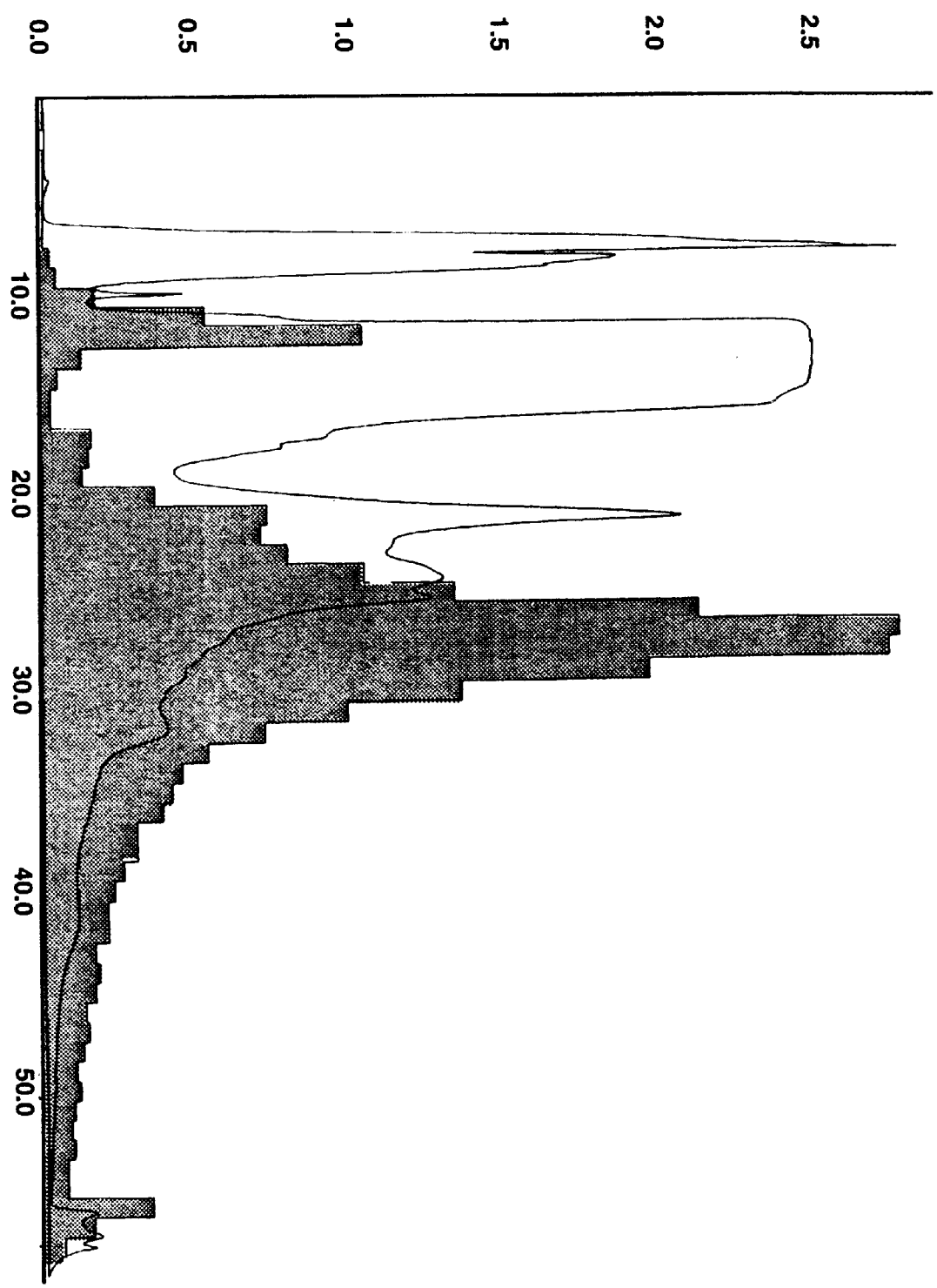
FIG. 5 Microbore biphenyl reverse phase HPLC (Vydac) resolving the deglycosylated p56 from N-glycanase and other contaminating A10 proteins.
Figure 6:
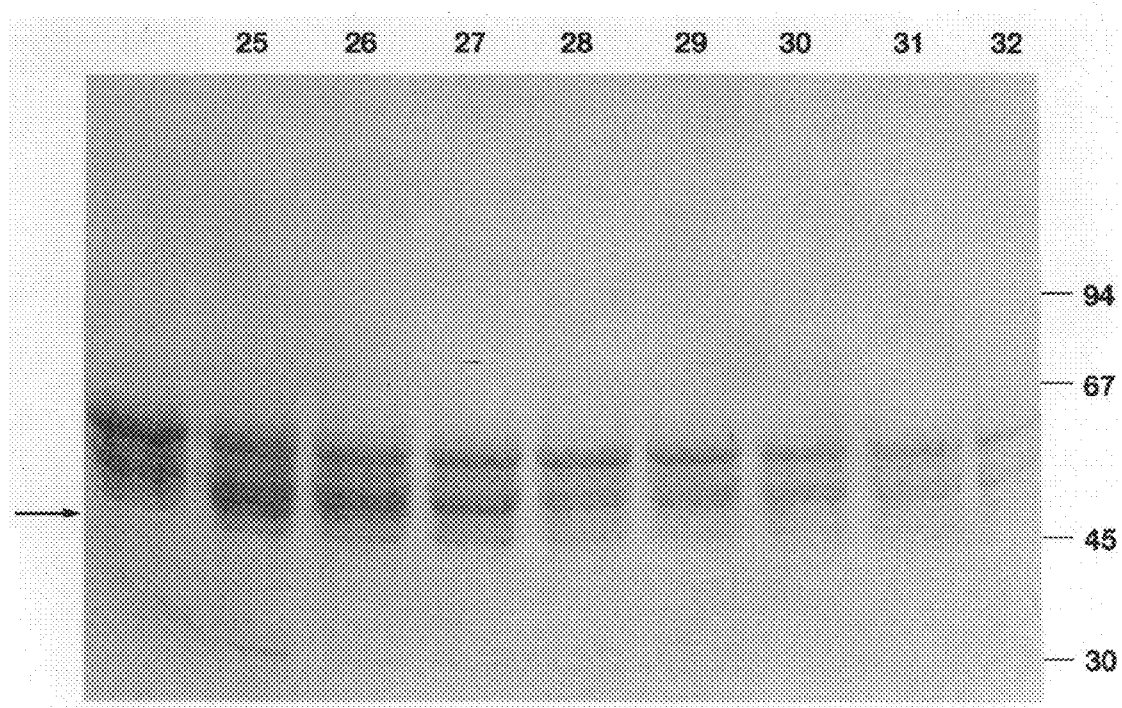
FIG. 6 Coomassie Blue staining of the proteins.

The pool is then subjected to microbore biphenyl reverse phase HPLC (Vydac) to resolve the deglycosylated p56 from N-glycanase and other contaminating A10 proteins, as shown in FIG. 5. FIG. 5 shows the absorbance (unshaded) and the radioactivity (shaded) of the fractions (Y axis) versus the retention time (X axis) resulting from this final HPLC resolution step. This figure shows that additional resolution of p56 is obtained since the net radioactivity (fractions 25–32, shaded plot) is resolved from the major contaminating proteins (depicted by absorbance at 215 nm, unshaded plot). Individual fractions containing deglycosylated p56 (same figure, fractions 25–32) were subjected to SDS PAGE and blotted onto PVDF. The results of this experiment are shown following staining the proteins on the blot with Coomassie Brilliant Blue R-250, see FIG. 6. The arrow in the figure depicts the location of deglycosylated p56, whose identity was confirmed by detection of radioactivity using phosphorimaging (data not shown). To prepare the segment of the blot containing deglycosylated p56 for microsequencing, the section representing the radiolabelled band was cut out of the PVDF paper. To verify that the band was indeed excised correctly, the remaining PVDF paper was reanalyzed by phosphorimaging to confirm that the radioactive band had indeed been selected precisely.

N-Terminal Sequence Analysis of p56.

Following deglycosylation and PVDF blotting, see P. Matsudaira (1987) *J. Biol. Chem.* Vol. 262, pp. 10035–10038, a peptide sequence was obtained (Glu-Pro-Arg-Ala-Pro-Pro-Glu-Lys-Ile-Ala-Ile-Val-Gly-Ala-Gly-Ile-) SEQ. ID. NO. 1 for a sample that was clearly in the picomolar range, see Table I below for yields per sequencing cycle. Thus, the amount of protein which was sequenced is estimated at 0.68 picomoles (from a minimum of 48 plates of A10 cells) based on the first cycle of sequencing. For a protein having a molecular mass of 52,000 daltons, this represents a yield of 0.7 nanograms from each plate of A10 cells. This value for the protein yield is based on the accumulation of all purification steps, using as an assay the radiolabelled p56 protein, for which an efficiency of labelling by the photoactivatable cyanoguanidine was estimated at 0.05%. The yield, then, does not necessarily represent the actual amount of p56 expressed in A10 cells.

The peptide sequence obtained is not only the putative amino terminal of p56, but also a "unique" sequence, not observed in protein sequence databases. In a general search of proteins showing identity to the p56 N-terminal peptide, no homology was noted to any mammalian potassium channel protein. A polyclonal antibody against the N-terminus of the protein was created to verify the conclusion that the sequence of the polypeptide was the same as the sequence of the N-terminus of the protein. Table I, next page,

TABLE I

| N-Terminal Sequencing of Deglycosylated p56 | | |
|---|---|---|
| Residue # | Amino Acid | Quantity (pmoles) |
| 1 | Glu | 0.68 |
| 2 | Pro | 0.39 |
| 3 | Arg | 1.50 |
| 4 | Ala | 1.40 |
| 5 | Pro | 1.46 |
| 6 | Pro | 1.54 |
| 7 | Glu | 0.93 |
| 8 | Lys | 0.46 |
| 9 | Ile | 1.06 |
| 10 | Ala | 1.29 |
| 11 | Ile | 1.14 |
| 12 | Val | 1.60 |
| 13 | Gly | 1.13 |
| 14 | Ala | 1.11 |
| 15 | Gly | 1.02 |
| 16 | Ile | 0.62 |

Development of a Polyclonal Antibody to the N-Terminus of p56.

The peptide representing the N-terminus of the N-deglycosylated p56 was synthesized, EPRAPPEKI-AIVGGC SEQ. ID. NO. 2 (see Formula 2 below), terminal GGC added to aid conjugation to KLH, the sequence without the terminal GGC is SEQ. ID. NO. 3, and used for immunization of a single rabbit.

H-Glu-Pro-Arg-Ala-Pro-Pro-Glu-Lys-Ile-Ala-Ile-Val-Gly-Gly-Cys-OH

●3CF$_3$—COOH                                   Formula 2

The first antigen dose was administered subcutaneously with Freunds complete adjuvant. After three weeks, an observable titer against the peptide (as measured by peptide conjugated to ovalbumin) was detected, although no response to the p56 protein was noted by Western blotting at any dilution of the serum. At this point, the antigen was administered subcutaneously with Freunds incomplete adjuvant, a process continued for at least half a year.

After the second bleed (6 weeks), a response was detected against p56 on Western blots (using partially purified as well as crude lysate material). Subsequently, all production bleeds of this single rabbit have yielded antibody with high titers against rat A10 p56. We have termed this serum antibody, which is defined as containing one or more IgG's specific for the N-terminal 12 amino acids of rat A10 p56, UP76.

Importantly, the bands immunodetected on blots were exactly coincident with the radioactivity profile noted by phosphorimaging. To demonstrate that the peptide sequence was derived from p56, purified samples of p56 were deglycosylated with N-glycanase and analyzed by Western blotting. Conclusively, both before and after deglycosylation, the radiolabelled protein was exactly coincident with the immunodetected band. This observation eliminated the possibility that the sequence obtained was from a 50–52 kD contaminating protein rather than from p56 itself.

Figure 7:
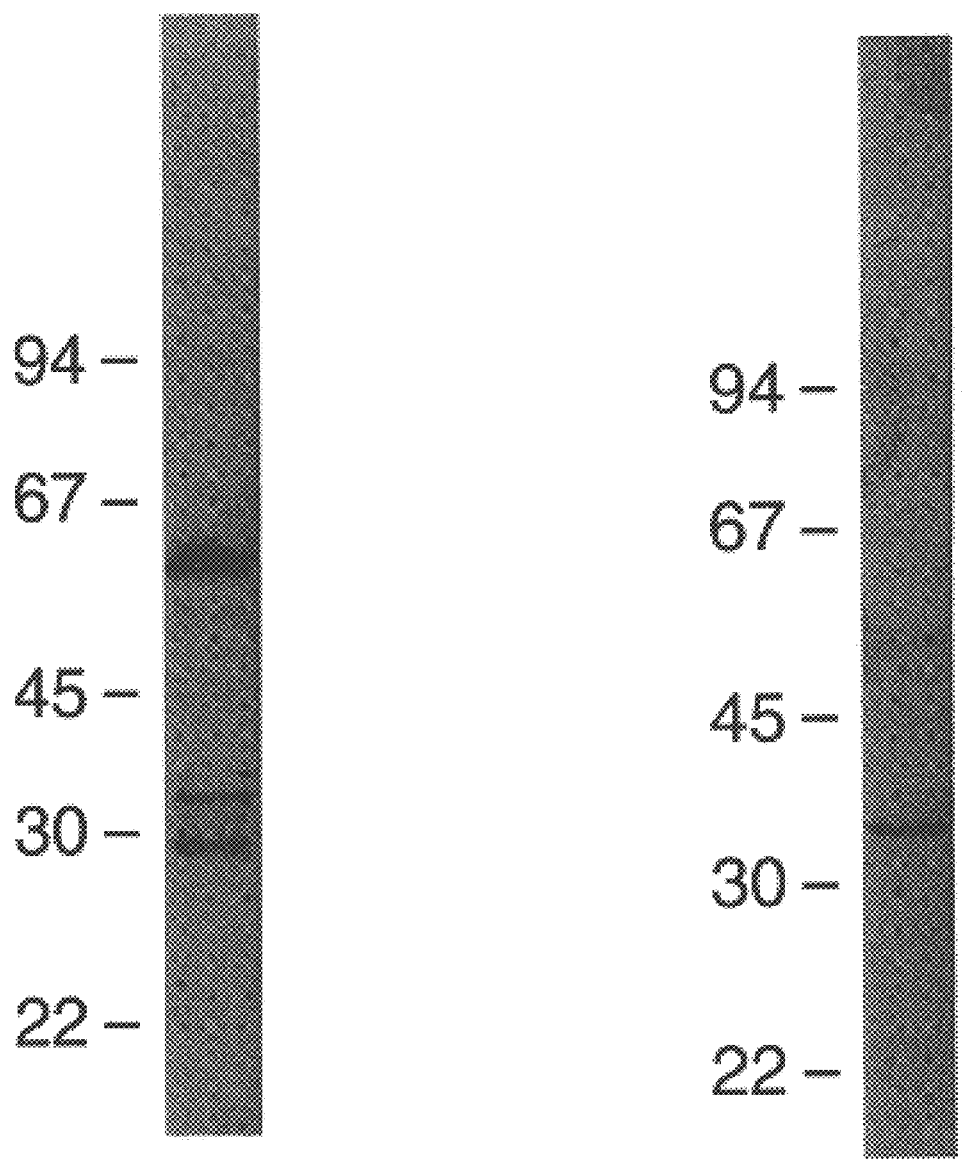
FIG. 7 Western blots showing the specific nature of antibody binding.

To verify that the bands detected on Western blots were not due to a non-specific binding phenomenon, the response on blots was blocked by pre-incubation of the serum with the peptide as shown in FIG. 7. This Figure shows two Western blots of gels containing resolved photoaffinity-labelled crude A10 proteins. The left figure shows the results of probing one of the two duplicate blots with the anti-p56 serum. In this result one detects the presence of bands at 56 kD, at 30 kD, and at 35 kD. The right figure shows the results of probing one of the blots with peptide-competed anti-p56 serum. An analysis of the latter blot probed with peptide pre-adsorbed serum shows that the 56 and 30 kD bands are definitively peptide competed (since they are no longer detected on the blot), and thus contain the sequence shown in Formula 2. The band at 35 kD is not related to p56 since it is not competed by peptide (Formula 2), and is therefore the result of a non-specific interaction of the antibody with this unknown antigen. The above data indicate that the band at 30 kD, which contains an epitope which is competed with peptide (Formula 2), probably originated either through proteolytic truncation of p56 or as a separate gene product.

The N-terminus of p56 is species-specific since no cross-reactivity is observed, using the rabbit anti-rat p56 antibody defined above, versus murine p56. A murine cell line derived from brain smooth muscle was labelled with the photoprobe. When the solubilized membrane pool was examined by Western blotting, no band was observed at p56. Similarly, following dissection of various tissues from a mouse, Western blotting was used to locate p56. Again, no signal was detected for non-rat p56 samples. In an analogous manner, COS cell extracts also failed to exhibit a p56 protein which cross-reacts with the UP76 antibody. However, photolabelling of murine brain smooth muscle cells with N-(3-azido-5-iodophenyl)-N'-cyano-N"-(1,1-dimethylpropyl)-guanidine indicated the presence of a radiolabelled band in the p56 area. This suggests the N-terminus of p56 is species-specific as reflected by Western blotting with UP76, but that p56 is probably present in other species as suggested by the results of photoaffinity labelling.

The p56 protein is present in the kidney, brain, trachea, and pancreas of rats. Utilizing the UP76 polyclonal antibody, described above, the extracts of various tissues from a dissected rat were examined by Western blotting. Both the soluble pools as well as the membrane pools (detergent solubilized) were used for these experiments. By Western blotting, bands at 56 kD and 30 kD were observed for pancreas, brain, trachea and kidney, each of which was eliminated when the serum had been preadsorbed with the competing peptide, shown in Formula 2.

These data demonstrate, for the first time, the presence of p56 in tissues other than aortic smooth muscle. The presence of p56 in these tissues was also established by examination of the sensitivity of the p56 bands to deglycosylation with N-glycanase. In all cases, a shift from p56 to p52 was observed as expected and as noted for authentic p56 from A10 cell membranes. Immunoreactive p56 was also observed in commercially obtained frozen rat kidney and brain tissue extracts.

We have also purified the specific IgG fraction from the crude serum of UP76, the rabbit anti-rat p56 antibody using an immobilized form of the peptide antigen, (see Formula 2). Following binding of the total IgG pool to Protein A-Agarose, the IgG was eluted by dissociation at low pH. Following adjustment of the pH to neutrality, the IgG pool was incubated with an immobilized form of the peptide (formula 2). Following extensive washing to remove undesired IgG proteins, the specific peptide-binding IgG was eluted by low pH dissociation, neutralized to pH 7.5, and concentrated by ultrafiltration (Amicon). This specific antibody is being used for expression cloning attempts and to determine tissue and cell specificity.

We claim:

1. A glycoprotein of about 54,000 to 60,000 daltons, as measured by SDS PAGE gel, having a core protein mass (free of sugars) of about 51,000 daltons, as measured by SDS PAGE gel, purified from rat cells, and capable of binding with N-(3-azido-5-iodophenyl)-N'-cyano-N"(1,1-dimethylproply)-guanidine.

2. A glycoprotein of claim 1, having $K_{ATP}$ channel activity either by itself or in membranes with other $K_{ATP}$ channels.

3. A glycoprotein of claim 2, as measured by SDS PAGE gel of about 56,000 daltons.

4. A glycoprotein of claim 3, where the average mass of the individual sugars of the glycoprotein, as measured by SDS PAGE gel, is about 2,500 daltons.

5. A glycoprotein of claim 4, having at least three sites of N-linked glycosylation.

6. A glycoprotein of claim 5, comprising the N terminal sequence of sequence ID NO. 1.

* * * * *

SEQUENCE LISTING (1) GENERAL INFORMATION:

(iii) NUMBER OF SEQUENCES: 3

(2) INFORMATION FOR SEQ ID NO:1:

```
        (i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:1:

Glu Pro Arg Ala Pro Pro Glu Lys Ile Ala Ile Val Gly Ala Gly Ile
1               5                   10                  15

(2) INFORMATION FOR SEQ ID NO:2:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:2:

Glu Pro Arg Ala Pro Pro Glu Lys Ile Ala Ile Val Gly Gly Cys
1               5                   10                  15

(2) INFORMATION FOR SEQ ID NO:3:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:3:

Glu Pro Arg Ala Pro Pro Glu Lys Ile Ala Ile Val
1               5                   10
```